United States Patent [19]
Long et al.

[11] Patent Number: 5,556,397
[45] Date of Patent: Sep. 17, 1996

[54] COAXIAL ELECTROSURGICAL INSTRUMENT

[75] Inventors: Gary Long, Cincinnati; Michael Johnson, Milford, both of Ohio

[73] Assignee: Laser Centers of America, Cincinnati, Ohio

[21] Appl. No.: 329,342

[22] Filed: Oct. 26, 1994

[51] Int. Cl.⁶ .................................................. A61B 17/39
[52] U.S. Cl. ............................................. 606/48; 606/50
[58] Field of Search ........................................ 606/48, 50

[56] References Cited

U.S. PATENT DOCUMENTS

| | | | |
|---|---|---|---|
| 4,483,338 | 11/1984 | Bloom et al. | 606/50 |
| 4,538,612 | 9/1985 | Patrick, Jr. | |
| 4,548,207 | 10/1985 | Reimels | 606/50 |
| 4,674,499 | 6/1987 | Pao | 606/50 |
| 4,688,569 | 8/1987 | Rabinowitz | |
| 4,706,667 | 11/1987 | Roos | |
| 4,805,616 | 2/1989 | Pao | 606/50 |
| 4,823,791 | 4/1989 | D'Amelio et al. | |
| 5,009,656 | 4/1991 | Reimels | 606/48 |
| 5,013,312 | 5/1991 | Parins et al. | |
| 5,234,429 | 8/1993 | Goldhaber | |
| 5,277,696 | 1/1994 | Hagen | |
| 5,281,216 | 1/1994 | Klicek | |
| 5,300,069 | 4/1994 | Hunsberger et al. | |
| 5,330,470 | 7/1994 | Hagen | |
| 5,342,357 | 8/1994 | Nardella | |

OTHER PUBLICATIONS

"Safer Electrosurgery" information booklet by NDM, 3040 East River Road, Dayton Ohio 45401-0154.

"Informational product brochure on Elekrotom BiCut" device by Berchtold AmBh Co., P.O. Box 4052, D-7200 Tuttlingen, Germany.

Instructional Booklet titled "Hazards of Electrosurgery", pp. 1–12, published by Education Design of Denver, CO.

Essentials of Monopolar Electrosurgery for Laparoscopy, by Voyles et al.

"Education and Engineering Solutions for Potential Problems With Laparascopic Monopolar Electrosurgery" by Voyles et al., The American Journal of Surgery, vol. 164, pp. 57–62.

*Primary Examiner*—Lee S. Cohen
*Attorney, Agent, or Firm*—Lowe, Price, LeBlanc & Becker

[57] ABSTRACT

A coaxial electrosurgical instrument has an elongate inner electrode insulated from and contained coaxially within a hollow tubular elongate outer electrode. Both electrodes have respective distal end portions which are uninsulated and contactable simultaneously to tissue to be operated on. A controlled, high-frequency, potential difference is provided between the electrodes under the user's control when the uninsulated distal end portions thereof are simultaneously contacted to tissue. A high frequency, high density, electrical current is thus caused to flow substantially only through that part of the contacted tissue which lies between the contacting portions of the inner and outer electrodes. Tissue is readily and cleanly cut between the inner and outer electrodes applying a continuous, undamped high frequency voltage difference. Cauterization and coagulation of the contacted tissue between the inner and outer electrodes may be performed by applying a periodically damped frequency electrical potential difference between the inner and outer electrodes. The outer electrode is preferably formed to have an inclined end surface, and the cooperating inner electrode is advantageously formed with a distal end part inclined to enable hooking of selected tissue to perform the surgical operations with improved visibility to the user.

18 Claims, 5 Drawing Sheets

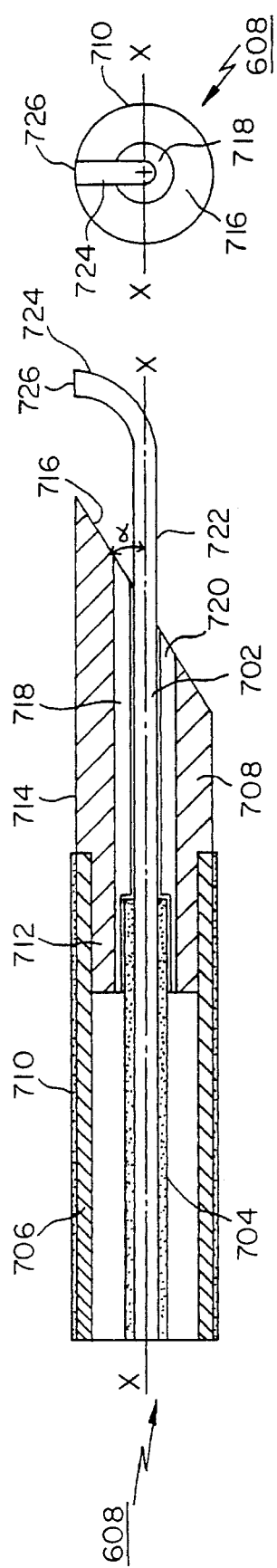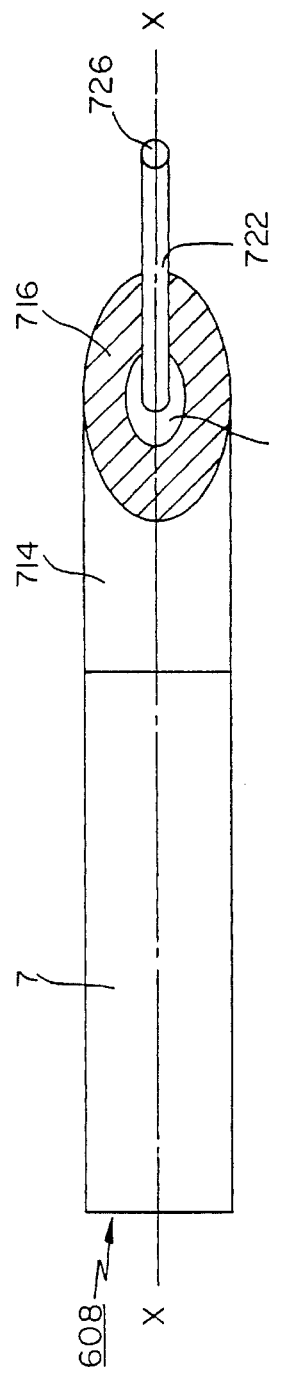
FIG. 7(A)
FIG. 7(B)
FIG. 7(C)

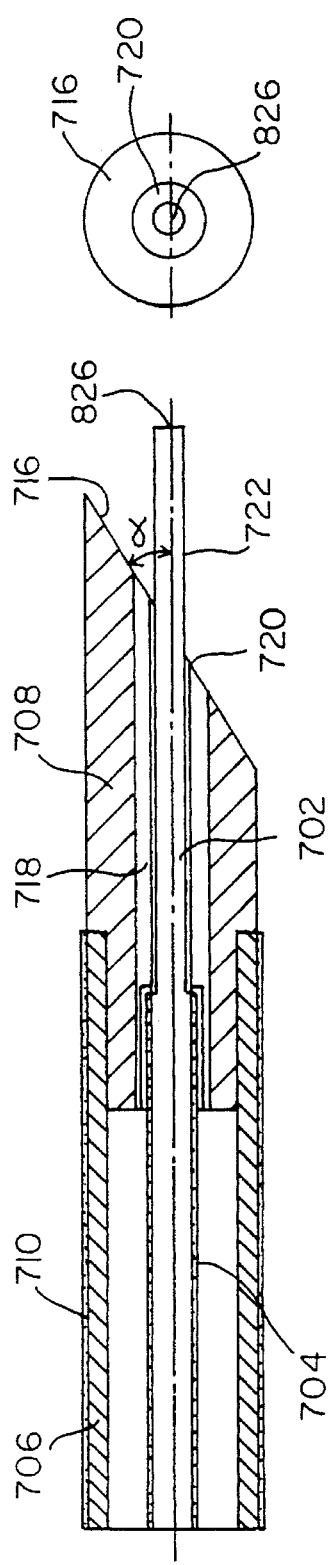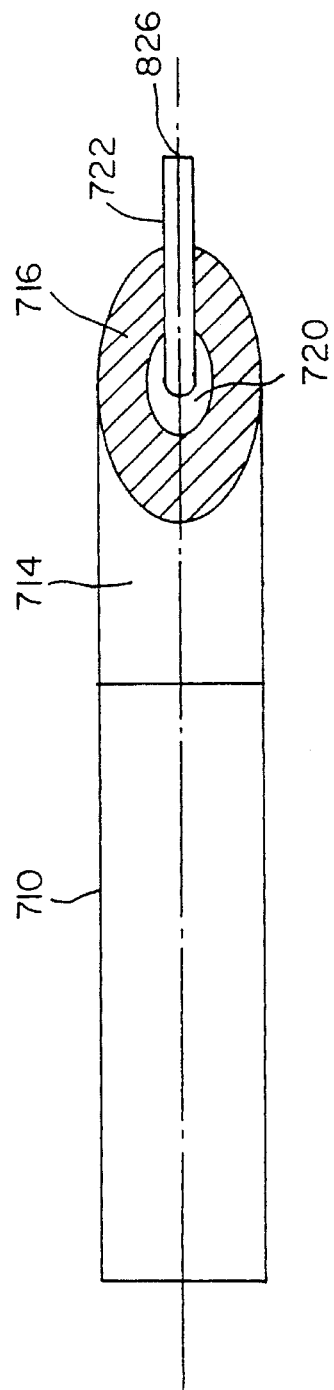
FIG. 8(A)
FIG. 8(B)
FIG. 8(C)

COAXIAL ELECTROSURGICAL INSTRUMENT

FIELD OF THE INVENTION

This invention relates to an electrosurgical instrument capable of performing incisions and coagulating and cauterizing functions, and more particularly to a coaxial electrosurgical instrument which performs like and can be used as easily as a monopolar surgical instrument but which eliminates current flow through the patient like a bipolar surgical instrument.

BACKGROUND OF THE RELEVANT ART

In recent times, the use of electrosurgical instruments to perform precise surgery has become widespread, mainly because it offers significant advantages over traditional scalpel surgery. For many surgical procedures, e.g., open heart surgery and laparoscopic procedures, electrosurgery results in significantly less patient trauma. In neurosurgical procedures, because of the very sensitive tissue around the surgical site and the need to immediately limit bleeding, the facility to perform incisions and coagulations with a single electrosurgical instrument is highly advantageous. Similarly, in transurethral surgery, where the goal is to safely remove unwanted or diseased tissue from a prostrate gland, the operation is best done with an electrosurgical instrument because the surgeon has to operate through a relatively narrow bore resectoscope.

It is well known that conventional electrosurgical instruments operate when an electrical path is completed between two electrodes. This requires that both electrodes be in some kind of contact with the patient's body. The electrical current provided to such instruments is sinusoidal, i.e., neither electrode is either positive or negative relative to the other except instantaneously.

Most surgeons prefer to use electrosurgical instruments over traditional scalpels because the former are essentially "bloodless" knives. Such an instrument can dissect tissue while at the same time reducing the amount of blood loss by permitting quick coagulation of the dissected tissue. Cutting occurs when the current density is high enough to explode the tissue cells near the electrode, and the same instrument may have a portion usable to either seal an incised vessel or to accelerate the coagulation process.

As best seen with reference to FIG. 1, when the sinusoidal waveform of the applied current is continuous and at its maximum amplitude, a cutting effect is obtained due to intense, almost explosive heating of cells contacted by the active electrode due to the locally very high current density. To provide coagulation, a damped current waveform, comprising short bursts of current rather than a continuous current, may be provided to the tissue. This causes local cellular dehydration because of the smaller amount of electrical current and power delivered to the tissue. It allows the surgeon to obtain hemostasis, allowing him to destroy tissue masses, or to cause selective desiccation of tissue. For a blended operation the surgeon may apply a current having a waveform as indicated at the right portion of FIG. 1.

As schematically indicated in FIG. 2, providing continuous high amplitude current via a thin electrode can generate a pure cut, and applying a damped waveform can generate a blended cut in which there is incision of tissue as well as coagulation of any blood leakage nearby. By selecting an appropriately shaped active electrode tip, applying a low power flow and holding the tip in physical contact with tissue, the surgeon can cause local heating and desiccation of the tissue without necessarily causing tissue necrosis. Finally, by holding the electrode close to, but not in direct contact with the tissue while applying a high power flow, a surgeon can cause arcing between the electrode and the tissue surface to cause local charring to produce fulguration. This last technique is commonly used in cardiovascular and thoracic surgical procedures.

A monopolar instrument is one in which the electrical current flows from the active electrode, which may be shaped as a blade, a hook, or a straight ended wire, to an electrical "ground". A grounding pad is typically applied to the thigh, back or some other spot on the patient's body where contact may be made with a relatively large surface area. Thus, in monopolar electrosurgical instruments, the surface area of one of the two electrodes is deliberately made significantly larger than that of the other. This is done so that the current density is much greater at the electrode having the smallest surface area when in contact with the patient's tissue. In such applications, the electrode with the smaller surface area is referred to as the "active" electrode. There are, however, serious problems that arise when there are strong current paths established due to deterioration of electrical insulation, capacitive coupling in spite of intact insulation, and accidental arcing between the instrument body and the patient's tissue in regions not visible to the surgeon. Some of these can be solved by the use of electrical shielding between the monopolar surgical instrument and a metal cannula. Monopolar electrosurgery, however, requires that an electric current flow through the patient's tissues away from the surgical site.

The frequency of the electrical voltage used for electrosurgery of any kind is typically much higher than the conventional mains frequency of 60 Hz, often in the range 400,000 Hz to 3,000,000 Hz, a range commonly referred to as "radiofrequency. Radiofrequency is generally considered too high to stimulate muscular tissue and, therefore, is believed to be safe to the patient. However, because the electrical current must flow through a significant portion of the patient's body, the surgeon and staff are at some risk of being shocked because of capacitive coupling with the patient. Also, the high voltage/high frequency generator and the wire leading therefrom to the active electrode, can act as an electrical noise generator and may adversely affect sensitive instrumentation.

In light of the above-described problems with a monopolar instrument, a bipolar instrument is sometimes used. It requires no grounding pad to be applied to the patient, but instead employs two electrodes which mechanically oppose each other like the two halves of a surgical forceps. The instrument is used to squeeze tissue between the two electrodes as a current passes between them to cause coagulation. Thus, a bipolar surgical instrument normally is used only when coagulation is desired and when current flowing through the patient is clearly undesirable. The bipolar instrument is not used to dissect tissue in most cases because it does not permit the surgeon to do so with precision.

Reference to FIG. 3 shows various types of monopolar active electrode tip shapes as well as the general tip end structure of a bipolar instrument. FIG. 4 illustrates the general overall configuration of a bipolar instrument.

FIGS. 5(A)–5(C) schematically indicate the typical distributions of electrical lines of force and equipotential lines normal thereto (as broken lines): for a monopolar instrument having a single electrode contacting the tissue to be operated on; for a bipolar instrument with two electrodes between which current flows through the patient's tissue, and for a coaxial surgical instrument (CSI) as in this invention in which there is a single electrode coaxially surrounded by an outer electrode with the entire operative electrical field highly localized and contained therebetween.

The present invention relates to a particularly advantageous form of a coaxial surgical instrument and has the general form illustrated in FIG. 6 and explained more fully hereinbelow.

SUMMARY OF THE INVENTION

It is a principal object of this invention to provide a coaxial electrosurgical instrument of simple form which alone enables a surgeon to selectively perform precise incisions, cauterization, and coagulation of a patient's tissue.

It is another object of this invention to provide a coaxial electrosurgical instrument which facilitates performance of precise incisions, coagulation of tissue and/or body fluids and sealing of blood vessels, by a user selectively engaging the same with an active electrode.

It is yet another object of this invention to provide an electrosurgical instrument suitable for laparoscopic surgery in confined or difficult locations within a patient's body without subjecting the patient's tissue to electrical currents except immediately at the surgical site.

It is a related object according to another aspect of this invention to provide a method of electrosurgically incising and/or selectively coagulating tissue during a surgical procedure with a single instrument.

It is another related object of this invention to provide a method by which a surgeon may perform incisions and/or coagulations with a coaxial electrosurgical instrument which facilitates clear and direct viewing of the surgical site, without passing electrical current through the patient's tissue except immediately at the surgical site.

These and other related objects of this invention are realized by providing a coaxial electrosurgical instrument which comprises an elongate, tubular, outer electrode covered with an insulating sleeve which leaves a distal end portion of the outer electrode uninsulated. An elongate inner electrode is located coaxially within the outer electrode and is electrically insulated therefrom. A distal uninsulated end portion of the inner electrode extends to a predetermined length from the distal uninsulated end portion of the outer electrode. This enables a user to make simultaneous electrical contact by the distal uninsulated end portions of both the inner and outer electrodes with the tissue to be operated on. Means are included for enabling the user to provide an alternating electrical voltage difference, at a controlled frequency, between the inner and outer electrodes. The distal end portion of the outer electrode preferably has a transverse end surface inclined at a first angle relative to a common axis of the inner and outer electrodes.

In another aspect of the invention there is provided a method which includes the steps of providing an elongate tubular outer electrode covered with an insulating sleeve which leaves a distal end portion of the outer electrode uninsulated, and also providing an elongate inner electrode located coaxially within the outer electrode. The two coaxial electrodes are electrically insulated from each other and a distal uninsulated end portion of the inner electrode extends to a predetermined length from the distal uninsulated end portion of the outer electrode. This enables the user to make simultaneous electrical contact by the distal uninsulated end portions of both the inner and outer electrodes with the tissue being operated on. The method includes the steps of providing an alternating electrical voltage difference at a controlled frequency between the inner and outer electrodes and applying the distal uninsulated end portions of both the inner and outer electrodes simultaneously to the selected tissue. This causes a high frequency, high density, current to flow through only that portion of the contacted tissue which lies between the applied inner and outer electrodes.

BRIEF DESCRIPTION OF THE DRAWING

FIG. 7(A) is a longitudinal cross-sectional view of the distal operating end of this invention according to the preferred embodiment, namely one in which the coaxial inner electrode has a bent end part; FIG. 7(B) is an external side view of the same portion of the instrument; and, FIG. 7(C) is an end view looking toward the electrodes in the same embodiment.

FIGS. 8(A), 8(B), and 8(C), are respective longitudinal cross-sectional, side and end views of a second embodiment of this invention, in which the inner electrode has an entirely straight end extending outwardly of the coaxial outer electrode.

DETAILED DESCRIPTION OF THE PREFERRED EMBODIMENTS

Figure 1:
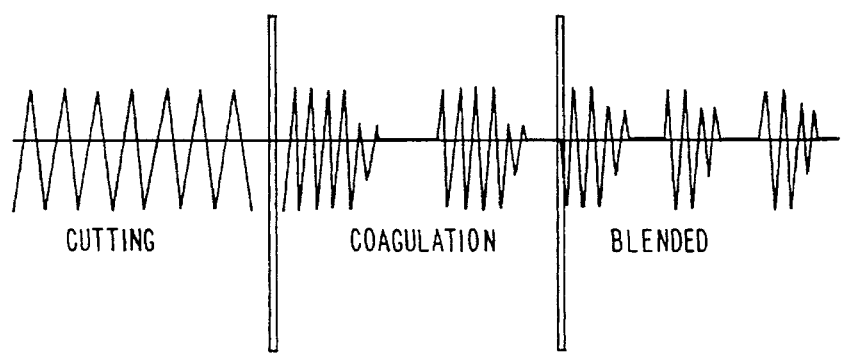
FIG. 1 is a graphical plot showing electrical current waveforms suitable for use during cutting, coagulation, and blended surgical operation with an electrosurgical instrument of any kind.
Figure 2:
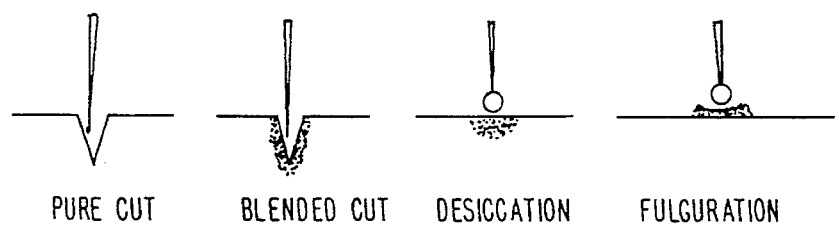
FIG. 2 shows in schematic form how differently shaped monopolar electrosurgical instrument tips may be used to perform a pure cut, a blended cut, desiccation of a tissue, or fulguration.
Figure 3:
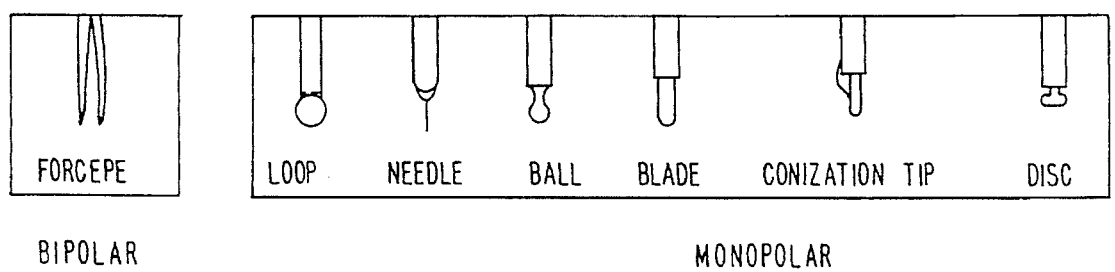
FIG. 3 shows exemplary active electrode tip shapes for monopolar and bipolar electrosurgical instruments of known type.
Figure 4:
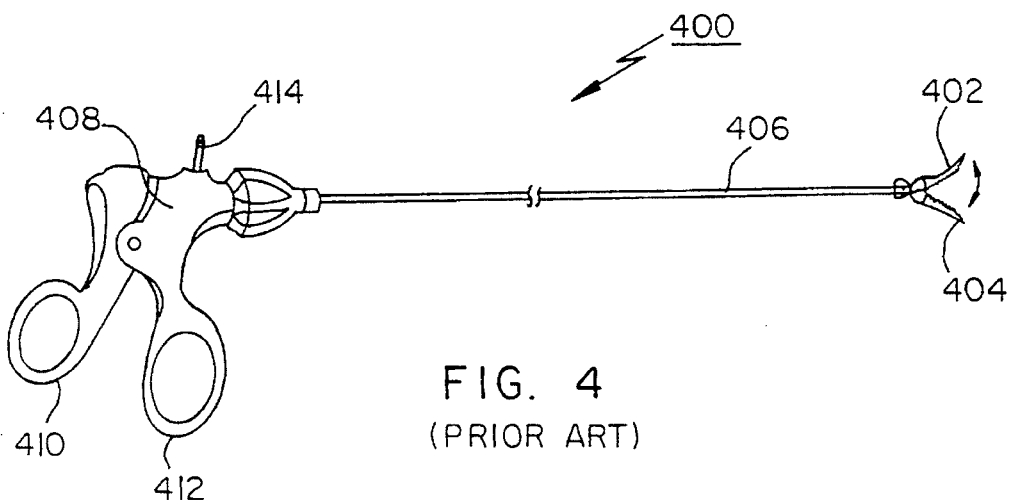
FIG. 4 is a side view of a bipolar electrosurgical instrument of known type.

FIG. 4 illustrates in side view a known bipolar electrosurgical instrument 400 which comprises two coacting and pivotably related elements 402 and 404, mounted at a distal end of an elongate tubular body element 406. A proximal end of this elongate body 406 is coupled to a hand-held, user-graspable, scissors like handle 408. Handle 408 comprises two pivotably cooperating elements 410 and 412 connected by suitable linkages to obtain corresponding pivoting movement between electrode elements 402 and 404 in known manner. Note cable 414 which, in use, would be connected to a source of controlled electrical power input and has individual wires connected to electrode elements 402 and 404.

Figures 5A, 5B, 5C:
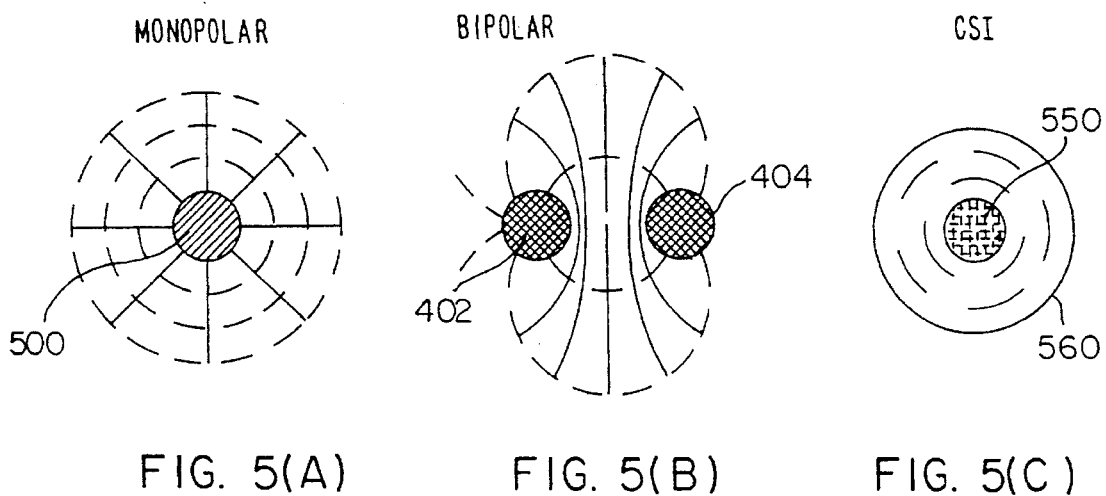
FIGS. 5(A)–5(C) present schematic views of the distributions of electric lines of force and equipotential lines for monopolar, bipolar, and coaxial surgical instruments (CSI), respectively.

FIG. 5(A) schematically illustrates by solid lines an electrical field about the single electrode 500 of a monopolar electrosurgical instrument. The electric field and time-varying electric currents extend through the tissue of the patient away from the single electrode 500. The electric lines of force are shown as solid lines and the equipotential lines as broken lines.

For a bipolar electrosurgical instrument comprising two cooperating electrodes, for example 402 and 404, when both electrodes are in contact with the patient's tissue, the (solid) electric lines of force between these two electrodes and the equipotential lines (broken) are as best seen in FIG. 5(B). Of necessity, electric current will tend to be experienced by the patient's tissue at locations away from the cooperating electrodes 402 and 404.

Finally, with a coaxial electrosurgical instrument comprising an inner electrode 550 and a coaxially surrounding outer electrode 560, the electric field is confined to be within the region between these two electrodes, as indicated in FIG. 5(C).

An advantage of the coaxial electrosurgical instrument is that it has a very limited region within which an electric current has to flow through a patient's tissue in order to perform its intended functions of incision, coagulation, or cauterization. Therefore, by making the respective diameters of the inner and outer electrodes small enough, a surgeon using the instrument can very severely limit the amount of tissue affected by electric current generated by contact with the electrodes at the operating distal end of the instrument. For neurosurgery, cardiovascular procedures, and the like, this is either highly desirable or, in some cases, vital.

Figure 6:
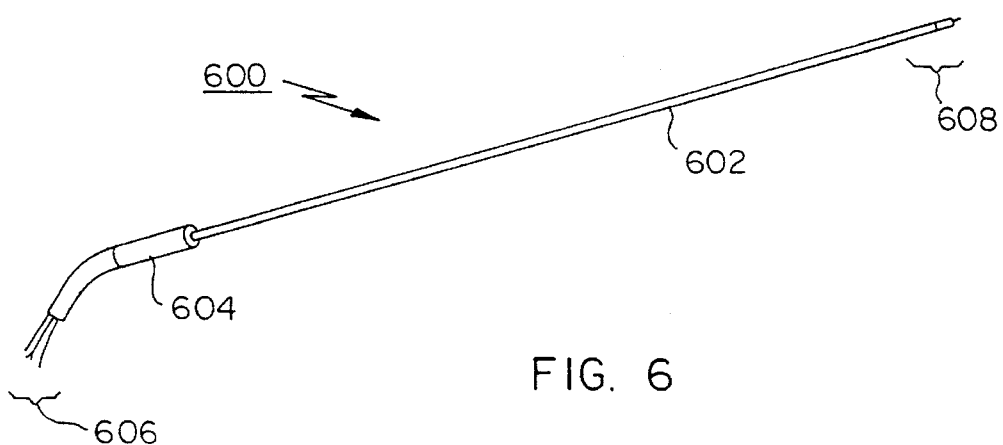
FIG. 6 is a side view of a coaxial electrosurgical instrument according to a preferred embodiment of this invention.

As best seen in FIG. 6, the coaxial electrosurgical instrument 600 according to this invention has a long, thin tubular body 602 (much like the elongate body 406 of the bipolar instrument 400 illustrated in FIG. 4) but a much simpler hand-held, user- graspable handle 604 through which electrical wiring 606 provides electrical power to the distal operating end 608 of the instrument. In use, therefore, a surgeon would hold the handle 604 and, by any conventional means, e.g., a thumb, foot, or otherwise operated switch, control the intensity, waveform, and duration of an electrical power supplied to the operating electrodes. This is discussed in greater detail in the following paragraphs.

FIGS. 7(A), 7(B) and 7(C) are related to a preferred embodiment of this invention, and provide a detailed understanding of the operating end portion 608 of an instrument like that illustrated generally in FIG. 6. It should be appreciated that the actual instrument may be several inches long, and that means of any suitable known type for controllably providing electrical power may be employed. In other words, it is the structure and functionality of the distal operating end of the instrument which is of significance and provides distinct advantages over the prior art. The manner of connecting the electrical power supply and controlling the electrical power flow therefore may be of known type and, while important, are not considered determinative of the novelty of this invention.

As best seen in FIG. 7(A), the distal end portion 608 of the preferred embodiment has a substantially coaxial structure around elongitudinal axis X—X. This structure includes a cylindrical, wire-like, electrically conductive inner electrode 702 coaxial about axis X—X. For most of its length along the instrument 600, inner electrode 702 is provided with an electrically insulating sleeve 704 to ensure against electrical shorting with respect to other elements.

Around the same axis, and coaxially surrounding inner electrode 702, is a conductive outer electrode 706 having the form of a thin elongate tube. At the distal end of outer electrode 706 there is fitted an electrically conducting tip element 708 which may be press-fitted or otherwise made virtually integral with the tubular structure of outer electrode 706. An insulating sleeve 710 is provided over the outer cylindrical surface of outer electrode 706 at least to the very end where the tubular outer electrode body 706 ends fitted tightly to tip element 708.

Tip element 708 is generally cylindrical and has a reduced diameter portion 712 sized and shaped to be fitted to the end of tubular outer electrode 706 in intimate electrical contact therewith. Tip element 708 also has an uninsulated exposed end portion 714 which preferably has the same outer diameter as tubular body 706, although this is not essential.

Tip element 708 is preferably cut at its end so as to have an inclined end face 716 which makes an acute angle "α" with respect to central axis X—X. As a consequence, end face 716 has a generally annular elliptic shape, as best seen in the view of FIG. 7(B).

The inside diameter of tip element 708 is made larger than the outside diameter of insulating sleeve 704 provided around inner electrode 702. An insulating cylindrical insert 718 is press fitted into tip element 708 and is shaped at its inner end so as to receive an extreme distal end portion of insulating sleeve 704 surrounding most of the length of inner electrode 702. Insert 718 is formed at its outermost end so that it has an angled face coplanar with the angled end face 716 of tip element 708. Therefore, closely surrounding the extreme distal end portion of inner electrode 702 there is the inclined end face 720 of insulating central insert 718 which virtually acts as a sliding journal bearing for the distal end portion of inner electrode 702.

Projecting outwardly of the plane of end faces 720 and 716 is a predetermined length 722 of inner electrode 702 which is straight and coaxial with axis X—X.

As best seen in FIGS. 7(A), 7(B) and 7(C), in the preferred embodiment this projecting portion of the inner electrode 702 is bent so that an extreme end part 724 thereof is virtually at 90° with respect to access X—X. The exact shape of the bend or curve involved is considered a matter of design choice, the key being that there is a sufficient length of portion 724 to enable a user to hook a portion of the tissue which is to be operated on by the device.

In the preferred embodiment per FIGS. 7(A), 7(B) and 7(C), this end part 724 of inner electrode 702 ends in an end face 726 which does not extend radially, relative to axis X—X, any further than the outside surface of tip element 708. In the preferred embodiment, tip element 708 has the same external diameter as the outer surface of the outer electrode 706. This is only the preferred structure, and persons of ordinary skill in the art may be expected to cause the end part 724 to be somewhat shorter or somewhat longer depending on particular applications of interest. There are certain advantages to the preferred embodiment as illustrated in FIGS. 7(A), 7(B) and 7(C), as discussed more fully hereinbelow.

Another structurally somewhat simpler embodiment is illustrated in FIGS. 8(A), 8(B) and 8(C). The only significant difference between this second embodiment and the preferred embodiment per FIGS. 7(A), 7(B) and 7(C) lies in the fact that in the second embodiment the inner electrode is entirely straight all the way through to its end face 826 which is preferably at right angles to the common access X—X. All the other elements, particularly the insulating sleeves 704 and 710 (of the inner and outer electrodes 702 and 706, respectively), the tip element 708, and the like are exactly the same in shape and function as in the preferred embodiment according to FIGS. 7(A), 7(B) and 7(C). Thus, insulating insert 718 in both embodiments has an angled end face 720 coplanar with the angled end face 716 of tip element 714, and serves as an insulating sliding journal bearing for inner electrode 702.

The only distinction between the two embodiments, in terms of structure, is that the preferred embodiment per FIGS. 8(A), 8(B) and 8(C) does not have a bent end part.

A detailed discussion will now be provided of the advantageous manner in which preferred embodiment per FIGS. 7(A), 7(B) and 7(C) may be employed in surgery in a very confined space, as in a laparoscopic procedure where finely controlled incisions to a predetermined small depth must be made. An example is where there is trauma or disease which requires very careful isolation of portions of organs physically close to a small bowel in a person's abdomen. Careless incision can cause bleeding and peritonitis, and improper use of monopolar or bipolar surgical instruments can result in damage to fragile tissues. It is in circumstances like these that the preferred embodiment provides unique advantages.

Figure 9:
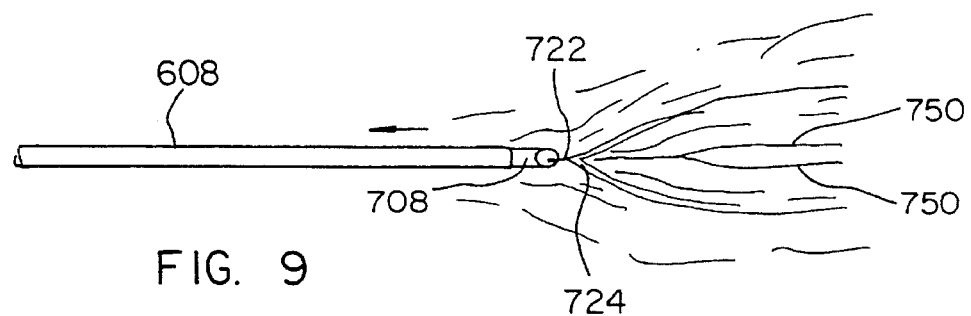
FIG. 9 is a view schematically illustrating how the bent end of the inner electrode according to the preferred embodiment per FIGS. 6, 7(A), 7(B) and 7(C) may be used to make an incision into tissue, with the operating inner electrode distal end part and the tissue being cut thereby clearly visible.

As best seen in FIG. 9, the surgeon applies a downward pressure on tissue with the outer surface of tip element 708 and a pulling force simultaneously to the body 608 of the coaxial electrosurgical instrument per the preferred embodiment, with the angled face 716 uppermost where it can be viewed easily. The extended portion 722 of the inner electrode is then pointing away from the surgeon and bent part 724 thereof is pressing into the tissue which is to be incised.

Figure 10:
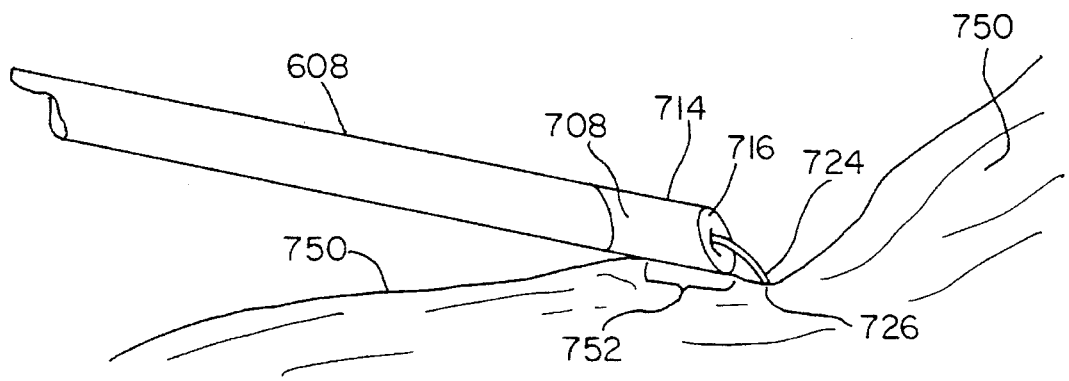
FIG. 10 is an enlarged perspective view of the operating end of the preferred embodiment, in use, either at the initiation of a cutting operation or as it would be used to provide local coagulation or catherization.

As best seen with reference to FIG. 10, the end part 724 of inner electrode 702 is then making electrical contact at its end surface 726 with tissue 750. In the just-described disposition of the elongate body 608 of the instrument, a lower portion of the outer surface of tip element 708 is pressed to the tissue at the side where inclined face 716 makes an acute angle with the outer cylindrical surface thereof, and a small zone 752 of the tissue is depressed. There is good electrical contact between the conductive tip element 708, i.e., the outer electrode in effect, and simultaneously by the bent part 724 of inner electrode 702.

When the surgeon now applies a controlled potential difference between the electrodes, a current will flow through only that portion of the tissue which is located between the inner and outer electrodes. Since this tissue is already under physical pressure due to contact at 752, a clean narrow incision may be made by providing a suitable electrical power flow. This is indicated generally in FIG. 9. The result is that the tissue 750 is incised by the very high current density immediately between the bent part 724 of the inner electrode and the adjacent angled surface 716 which is part of the outer electrode.

It is important to appreciate the fact that because the applied potential difference is of a time-varying oscillating nature, neither the inner electrode 702 nor the outer electrode 706 is permanently positive or negative relative to the other. The high frequency electrical potential difference between the electrodes, when both are in conductive contact with the tissue, will result in a corresponding time-dependent electrical current flowing between the end part 724 and the inclined surface 716, respectively, of the inner and outer electrodes 702 and 706.

In the structure illustrated in the above-described figures, it is clear that the uninsulated exposed outer surface area of the outer electrode, essentially the cylindrical surface 714 and the end face 716 of the tip element 708, is considerably larger than the uninsulated area of the exposed straight portion 722 and the bent part 724 (including end face 726) of the inner electrode 702. Because of this disparity in surface area sizes, the current density immediately surrounding the bent part 724 and the end face 726 of the inner electrode 702 will be very high and will cause explosive disruption of the contacted tissue cells, resulting in clean hemostatic cut, provided electrical power is delivered in an amount and at a frequency suited to the particular tissue. In other words, to make the same cut through a denser tissue may require a higher power input or frequency as compared to, say, a softer and more moisture-laden tissue. The exact values of the current electrical power and the frequency at which it is delivered must be matters of choice for the surgeon in light of exigent circumstances.

As will be readily appreciated, the surgeon could turn the tool 180° relative to the above-described mode of application, so that a patient's tissue is contacted by the outer surface 714 of tip element 708, i.e., by the outer electrode 706, as well as by the curved outer surface the bend in the uninsulated portion of the inner electrode 702. There would be no hooking of the tissue under these circumstances, but upon delivery of the right amount of electrical power at the right frequency a surgeon may be able to make incisions. The difference is that in the first-described disposition it was the narrow leading wedge-shaped portion of the tip element 708 which depressed the tissue at 752 and allowed the surgeon a clear view of how and where the bent part 724 of the inner electrode was performing its cutting function.

As noted earlier, it is well known that by appropriate control on the electrical power delivered, and/or the frequency at which the current is generated, the same electrode may be used to coagulate tissues and/or any bodily fluids present contacted. Similarly, by appropriate variation of the electrical power and/or the frequency at which it is provided, cauterization of vessels carrying bodily fluids may be obtained.

Figure 11:
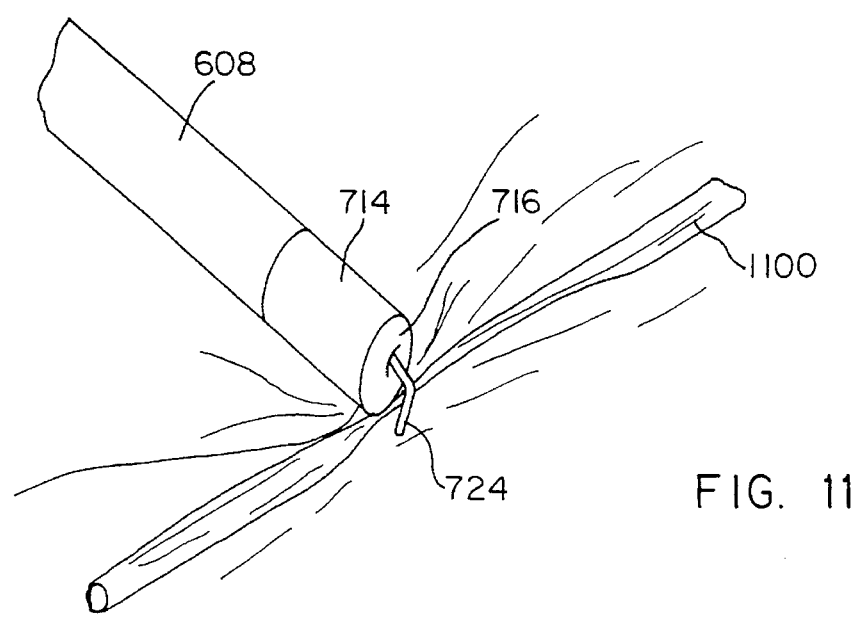
FIG. 11 is a further enlarged view of the preferred embodiment to illustrate a manner of its use to hook a blood vessel in a patient to apply energy to cauterize the same.

FIG. 11 illustrates one such procedure with the preferred embodiment per FIGS. 7(A), 7(B) and 7(C). In this application, the surgeon employs the bent part 724 to hook over a blood vessel 1100. By tugging on the blood vessel in this manner, the surgeon can cause local collapse of the walls of the vessel and, by appropriate delivery of electrical power generate a local electrical burn and sealing of the vessel. By doing this at two points, and thereafter incising therebetween at a higher power rate or frequency, the surgeon can cut through the vessel without permitting leakage of its contents at the surgical site. These and other variations will become readily apparent to surgeons utilizing the tool as they gain greater familiarity with its effectiveness.

The second embodiment per FIGS. 8(A), 8(B) and 8(C can be used to perform substantially the same sort of functions of incision, coagulation, and cauterization as described with respect to the preferred embodiment per FIGS. 7(A), 7(B) and 7(C). The only distinction is that there is no bent part with which to hook tissue, so that there has to be pressure applied by the outer cylindrical surface of that portion of the inner electrode 702 which extends beyond the inclined end face 716 of the outer electrode, i.e., the tip element 708 thereof. Thus, with the second embodiment it would not be possible for a surgeon to hook a blood vessel as was possible with the first embodiment as just described with reference to FIG. 11. Nevertheless, for certain types of operations a surgeon may wish to perform incisions of very limited depth without running the risk of accidentally hooking a fine blood vessel or tissue weakened by disease or trauma. For such applications, and with obvious variations of circumstances, it may be preferable to use the second embodiment per FIGS. 8(A), 8(B) and 8(C).

When either embodiment is used in laporscopic surgery, conventional fiber optic viewing instruments, TV monitors, view enlargement devices or the like may be used exactly as with monopolar or bipolar instruments of known kind.

Both inner electrode 702 and outer electrode 706, as well as tip element 708, may be made a non-corrodible metal such as stainless steel. Insulating sleeves 704 and 710, as well as insulating insert 718, may be made of a known chemically inert electrically insulating material such as Teflon™ or nylon.

Experimental tests and theoretical analysis lead to the conclusion that making the tissue-contactable uninsulated surface area of the inner electrode 702 at least less half the corresponding tissue-contactable uninsulated area of the outer electrode 706 (i.e., the surface corresponding to its integral tip-element 708) will ensure good current density.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A coaxial electrosurgical instrument for performing surgical procedures on tissue, comprising:

an elongate, tubular, outer electrode covered with an insulating sleeve which leaves a distal end portion of the outer electrode uninsulated;

an elongate, inner electrode, located coaxially within the outer electrode and electrically insulated therefrom such that a distal uninsulated end portion of the inner electrode extends to a predetermined length from the distal uninsulated end portion of the outer electrode to enable simultaneous electrical contact by the distal uninsulated end portions of both the inner and outer electrodes with the tissue to be operated on; and means for providing an alternating electrical voltage difference at a controlled frequency between the inner and outer electrodes;

wherein the distal end portion of the outer electrode has a transverse end surface inclined at an acute first angle relative to a common axis of the inner and outer electrodes.

2. The coaxial electrosurgical instrument according to claim 1, wherein:

the distal uninsulated end portion of the inner electrode has a first surface area which is less than a second surface area of the distal uninsulated end portion of the outer electrode.

3. The coaxial electrosurgical instrument according to claim 2, wherein:

a ratio of the first surface area to the second surface area is less than 1:2.

4. The coaxial electrosurgical instrument according to claim 1, wherein:

the distal uninsulated end portion of the inner electrode over all of the predetermined length thereof is straight.

5. The coaxial electrosurgical instrument according to claim 1, wherein:

the distal uninsulated end portion of the inner electrode includes an end part which is inclined at a second angle relative to the common axis.

6. The coaxial electrosurgical instrument according to claim 5, wherein:

the transverse end surface and an outer peripheral surface of the outer electrode intersect at an acute angle to form a leading edge portion of the outer electrode and the inclined end part of the inner electrode is turned toward the leading edge port ion of the outer electrode.

7. The coaxial electrosurgical instrument according to claim 6, wherein:

the second angle is approximately 90°.

8. The coaxial electrosurgical instrument according to claim 7, wherein:

the inclined end part of the inner electrode extends radially relative to the common axis no further than the leading edge portion of the outer electrode.

9. The coaxial electrosurgical instrument according to claim 8, wherein:

the distal uninsulated end portion of the inner electrode has a first surface area which is less than a second surface area of the distal uninsulated end portion of the outer electrode.

10. The coaxial electrosurgical instrument according to claim 9, wherein:

a ratio of the first surface area to the second surface area is less than 1:2.

11. A method of performing surgical operations including incisions, cauterizations and coagulations of a tissue, comprising the steps of:

providing an elongate, tubular, outer electrode covered with an insulating sleeve which leaves a distal end portion of the outer electrode uninsulated, the distal end portion having an end face inclined at an acute first angle to an axis of the outer electrode;

providing an elongate, inner electrode, located coaxially within the outer electrode and electrically insulated therefrom such that a distal uninsulated end portion of the inner electrode extends to a predetermined length from the distal uninsulated end portion of the outer electrode to enable simultaneous electrical contact by the distal uninsulated end portions of both the inner and outer electrodes with the tissue to be operated on;

providing an alternating electrical voltage difference at a controlled frequency between the inner and outer electrodes; and applying the distal uninsulated end portions of both the inner and outer electrodes simultaneously to the tissue to be operated to thereby cause a high frequency, high density, current to flow substantially only through that portion of the contacted tissue which lies between the applied inner and outer electrodes.

12. The method according to claim 11, wherein:

the alternating voltage difference is provided so as to have a continuous waveform at a selected single frequency, to thereby enable incision of the contacted tissue between the applied inner and outer electrodes.

13. The method according to claim 11, wherein:

the alternating voltage difference is provided so as to have a periodically damped waveform, to thereby enable a user selectively cauterize and coagulate the contacted tissue and any bodily fluids present between the applied inner and outer electrodes.

14. The method according to claim 11, wherein:

the distal uninsulated end portion of the inner electrode has a first surface area which is less than a second surface area of the distal uninsulated end portion of the outer electrode;

the distal uninsulated end portion of the inner electrode includes an end part which is inclined at a second angle relative to the axis; and the step of applying the distal end portions of both the inner and outer electrodes to the tissue includes a step of hooking a portion of the contacted tissue with the inclined end part of the inner electrode.

15. The method according to claim 14, wherein:

the alternating voltage difference is provided so as to have a continuous waveform at a selected single frequency, to thereby enable incision of the contacted tissue between the applied inner and outer electrodes.

16. The method according to claim 14, wherein:

the alternating voltage difference is provided so as to have a periodically damped waveform, to thereby enable selective cauterization and coagulation of the contacted tissue and any bodily fluids present between the applied inner and outer electrodes.

17. The method according to claim 14, comprising the further step of:

providing known viewing means to enable the user to view a region of the patient's body which includes the tissue being operated on, wherein the step of hooking tissue is performed so that the hooked tissue is positioned in a field of view of the user before and during performance of an operation on the hooked tissue.

18. The method according to claim 14, comprising the further step of:

applying the inclined end surface of the outer electrode against the tissue, for thereby selectively performing one of the functions of cutting, coagulating or cauterizing of the contacted tissue.

\* \* \* \* \*